(12) United States Patent
Theobald et al.

(10) Patent No.: US 9,220,691 B2
(45) Date of Patent: Dec. 29, 2015

(54) TRANSDERMAL THERAPEUTIC SYSTEM COMPRISING NORELESTROMIN FOR CONTRACEPTION AND HORMONE REPLACEMENT

(75) Inventors: Frank Theobald, Wehr (DE); René Eifler, Koblenz (DE)

(73) Assignee: LTS LOHMANN THERAPIE SYSTEME AG, Andernach (DE)

( * ) Notice: Subject to any disclaimer, the term of this patent is extended or adjusted under 35 U.S.C. 154(b) by 1336 days.

(21) Appl. No.: 12/446,887

(22) PCT Filed: Oct. 10, 2007

(86) PCT No.: PCT/EP2007/008797
§ 371 (c)(1),
(2), (4) Date: Feb. 3, 2010

(87) PCT Pub. No.: WO2008/049516
PCT Pub. Date: May 2, 2008

(65) Prior Publication Data
US 2010/0150993 A1    Jun. 17, 2010

(30) Foreign Application Priority Data
Oct. 26, 2006   (DE) .......................... 10 2006 050 558

(51) Int. Cl.
*A61K 31/567* (2006.01)
*A61P 15/18* (2006.01)
*A61K 9/70* (2006.01)
*A61P 5/34* (2006.01)
*A61K 31/565* (2006.01)
*A61K 31/57* (2006.01)

(52) U.S. Cl.
CPC ............. *A61K 9/7069* (2013.01); *A61K 31/565* (2013.01); *A61K 31/567* (2013.01); *A61K 31/57* (2013.01)

(58) Field of Classification Search
USPC ......................................................... 424/449
See application file for complete search history.

(56) References Cited

U.S. PATENT DOCUMENTS

| 4,454,159 | A | * | 6/1984 | Musher ......................... 514/17.2 |
| 4,973,468 | A | * | 11/1990 | Chiang et al. .................. 424/449 |
| 5,053,227 | A | * | 10/1991 | Chiang et al. .................. 424/448 |
| 5,662,926 | A | * | 9/1997 | Wick et al. ..................... 424/448 |
| 5,902,601 | A | | 5/1999 | Horstmann |
| 6,071,531 | A | | 6/2000 | Jona et al. |
| 2004/0202708 | A1 | * | 10/2004 | Roehrig et al. ............... 424/449 |
| 2006/0121102 | A1 | * | 6/2006 | Chiang ......................... 424/449 |
| 2008/0279915 | A1 | | 11/2008 | Wilhelm |

FOREIGN PATENT DOCUMENTS

| CA | 2 630 675 | 8/2007 |
| DE | 43 32 094 | 3/1995 |
| DE | 10 2006 026 060 | 7/2007 |
| WO | WO 96/40355 | 12/1996 |
| WO | WO 01/49273 | 7/2001 |
| WO | WO 2005/120470 | 12/2005 |
| WO | WO 2006/036899 | 4/2006 |
| WO | WO 2007/087872 | 8/2007 |

OTHER PUBLICATIONS

Center for Drug Evaluation and Research; Drug Labeling for ORTHO EVRA, Nov. 20, 2001.

* cited by examiner

*Primary Examiner* — Audrea Buckley
(74) *Attorney, Agent, or Firm* — Frommer Lawrence & Haug LLP

(57) ABSTRACT

The present invention relates to a transdermal therapeutic system for applying the active ingredient norelgestromin onto the skin, optionally in combination with estrogens. It further relates to the use of such systems for hormonal contraception, and for hormone replacement therapy.

9 Claims, 2 Drawing Sheets

TRANSDERMAL THERAPEUTIC SYSTEM COMPRISING NORELESTROMIN FOR CONTRACEPTION AND HORMONE REPLACEMENT

The present invention relates to a transdermal therapeutic system for administration of the active ingredient norelgestromin to the skin, optionally in combination with estrogens. It further relates to the use of such systems for hormonal contraception, and for hormone replacement therapy.

The active ingredient norelgestromin (17-deacyl-norgestimate; 13-ethyl-17-hydroxy-18,19-dinor-17-alpha-pregn-4-en-20-yn-3-one oxime) belongs as sex hormone to the class of progestogens. Norelgestromin inhibits the release of lutenizing hormone (LH) and thus has ovulation-inhibitory activity. One advantage of norelgestromin is that its androgenic effect is lower than that of the prodrug norgestimate or its other metabolites such as 3-ketonorgestimate and levonorgestrel. Estrogens inhibit the secretion of follicle-stimulating hormone (FSH) and thus inhibit ovulation. The estrogens include for example 17-beta-estradiol and ethinylestradiol. Products comprising norelgestromin, as well as combination products comprising norelgestromin and ethinylestradiol, are employed for contraception and for hormone replacement therapy in women.

Contraception is not a disorder in the conventional sense because, after all, it does not serve to treat a life-threatening or treatment-requiring pathological condition. Many women therefore wish to have a pharmaceutical form which makes administration possible in a discreet way and, if possible, avoids daily use, as is necessary with oral contraceptives. Thus, in the contraception sector there are to be found implants, vaginal rings but also transdermal systems which make substantially inconspicuous administration possible.

A disadvantageous effect of many novel administration forms such as, for example, implants, vaginal rings etc. is that the user frequently has insufficient trust in such pharmaceutical forms because, in contrast to tablets, it is not possible to be sure that the pharmaceutical form has been administered properly. This sense of reliability is very important for the user in particular in contraception therapy and significantly influences compliance.

Transdermal systems allow very discreet use and moreover a visual check of correct administration in the period of use. The success of the Ortho Evra™ TCS (transdermal contraceptive system, norelgestromin/-ethinylestradiol) shows that women accept this type of administration well.

A large number of transdermal therapeutic systems (TTS) for administering these active ingredients is already known in the state of the art. Such TTS typically have a structure composed of a support layer which is impermeable to medicinal substance, a reservoir layer which contains medicinal substance and a pressure-sensitive adhesive layer for attachment to the skin, it being possible for the latter to be identical to the reservoir layer containing the medicinal substance. The layer containing medicinal substance may also comprise further ingredients, e.g. plasticizers, tackifiers, solubilizers, stabilizers, fillers, carriers and permeation promoters. The pharmaceutically acceptable substances suitable for this purpose are known in principle to the skilled person.

Although transdermal therapeutic systems are known in principle as dosage forms, the formulation of a particular active ingredient, e.g. norelgestromin, as TTS represents a challenge. Various problems may arise. Thus, a TTS in order to be therapeutically usable must make a sufficiently high active ingredient flux through the skin possible. It must also exhibit good stability and may not undergo any changes in particular during storage. Selection of suitable polymers for the active ingredient reservoir may prove to be a problem because these polymers must be compatible with the respective active ingredient. A further requirement is that the TTS of the invention is that it can be manufactured at reasonable cost.

Such a system is described for example in U.S. Pat. No. 6,071,531. The formulation described therein consists of a non-acrylate-based polymer, an enhancer and a solvent, where the enhancer consists of the group of lactate esters with $C_{12}$-$C_{18}$ basic structure of aliphatic alcohols, propylene gylocol monolaurate and combinations of these substances. The Ortho Evra™ TCS which is commercially available in many countries of the world makes use for example of the teaching of this patent.

WO 2005/120470 A1 discloses a matrix-controlled transdermal therapeutic system with norelgestromin alone or in combination with an estrogen, in particular ethinylestradiol. A hotmelt adhesive, in particular a styrene block copolymer, is used for the matrix.

A disadvantage of the system available on the market (Ortho Evra™ TCS) is its relatively large application area of 20 $cm^2$, which makes use difficult.

It was therefore an object of the present invention to avoid the prior art disadvantages mentioned and to provide a transdermal therapeutic system for administering norelgestromin, optionally in combination with estrogen, which is better suited owing to an increased delivery rate of the active ingredient(s) for contraception or for hormone replacement therapy. It is moreover intended to achieve improved patient compliance through a simpler and more reliable application method. Use should in addition be as discreet as possible.

This object is achieved according to the invention by a transdermal therapeutic system (TTS) as claimed in claim 1, which includes a norelgestromin-containing, at least monolayer active ingredient reservoir based on silicone polymers. It has surprisingly emerged that in particular the combination of norelgestromin and ethinylestradiol with a substance or a combination of substances such as diethylene glycol monoethyl ether, butanediol or 1,2-propylene glycol, a substantially higher permeation through the skin can be achieved than in comparison with the Ortho Evra™ TCS available on the market. The formulation according to the invention shows distinctly higher levels of permeation through human skin epidermis over a predetermined period of 72 hours. The TTS formulations moreover have differing contents of norelgestromin and ethinylestradiol.

DETAILED DESCRIPTION OF EMBODIMENTS

Figure 1:
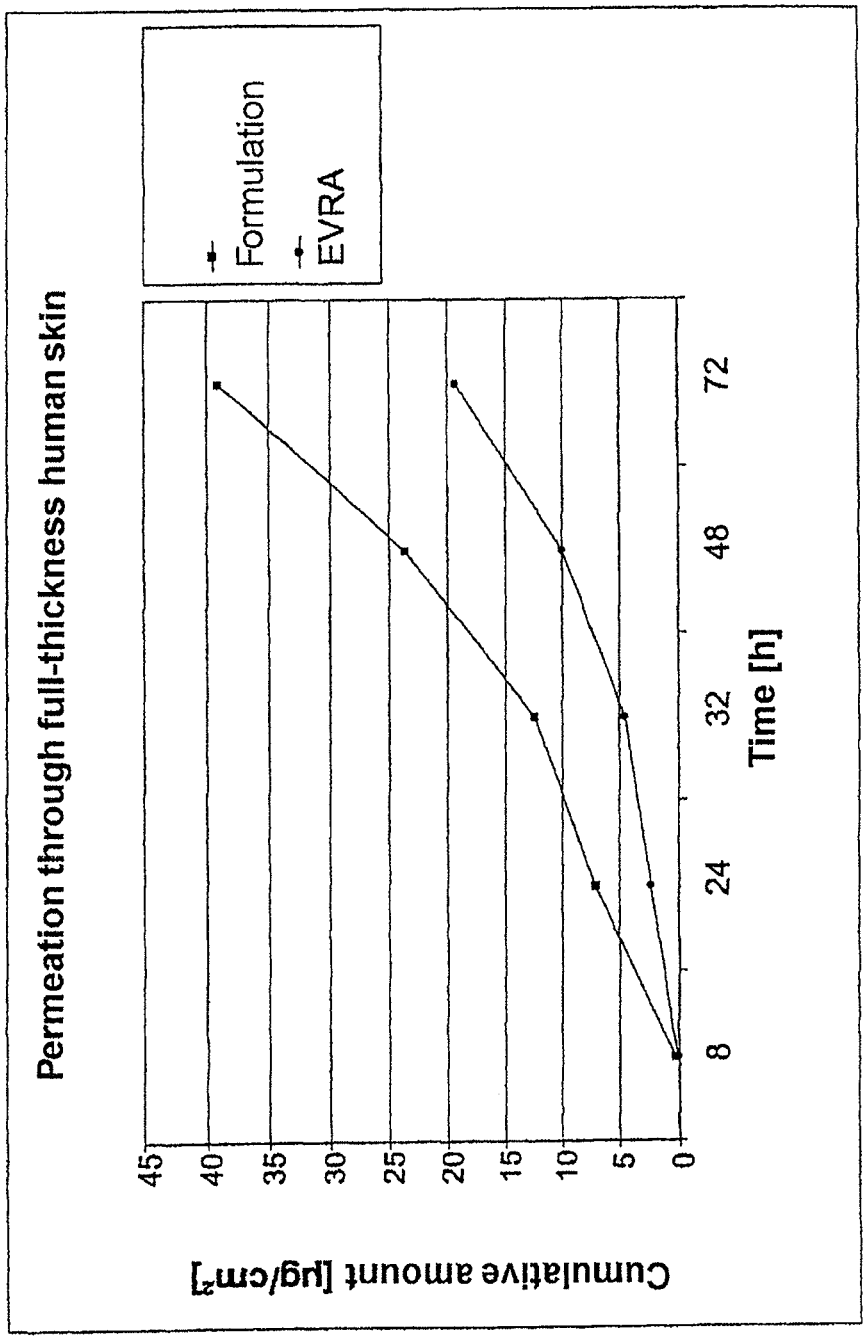
FIG. 1 depicts permeation of norelgestromin through epidermis of human skin.

The TTS of the invention can remain in place after application to the skin over a prolonged period, e.g. up to 7 days, and during this time deliver the active ingredient(s) to the skin in a controlled manner. The need for daily administration, as is the case with oral contraceptives, is avoided in this way. If necessary, the treatment can be terminated or interrupted in a simple manner by removing the TTS from the skin.

A particular advantage is that it is possible to employ in this way TTS with distinctly smaller application areas compared with application areas of Ortho Evra™ TCS, at identical permeation rates around 17%, preferably around 36%, particularly preferably around 48%. An easier manipulation and improved wearing comfort is associated therewith.

Addition of the abovementioned substances has the effect of bringing about a solubilization between the silicone matrix and the active ingredient. The use of diethylene glycol monoethyl ether is preferred. It has proved to be particularly advantageous when the proportion of the substances based on the matrix weight is from 1 to 80% by weight, preferably between 5 and 40% by weight.

Suitable silicone polymers which are used are silicones, polysiloxanes or silicones which may themselves have pressure-sensitive adhesive properties. Pressure-sensitive silicone adhesives mean pressure-sensitive adhesives for example based on a poly-dimethylsiloxane structure or poly-dimethyldiphenyl-siloxane structure. Commercially available pressure-sensitive silicone adhesives such as, for example, BIO-PSA from Dow Corning Corporation are suitable in particular. BIO-PSA Q7-4302 is preferably employed.

A TTS normally comprises an active ingredient-impermeable backing layer, one or more active ingredient-containing matrix layers, optionally a membrane which controls release of active ingredient, and a detachable protective layer, it being possible for the matrix layer to be self-adhesive or be additionally provided with a pressure-sensitive adhesive layer on the skin side.

The active ingredient reservoir is preferably composed of an at least monolayer polymer matrix which comprises the active ingredient norelgestromin and optionally further active ingredients such as, for example estradiol, ethinylestradiol or estriol. It is advantageously possible for further active ingredients with an agonistic effect on the estradiol receptor to be present. The transdermal therapeutic system may also consist of a plurality of active ingredient-containing matrix layers which may differ in their composition and/or active ingredient content.

The active ingredient matrix may, besides said polymers and active ingredients, additionally comprise further excipients such as plasticizers, tackifiers, solubilizers, stabilizers, fillers, carriers, permeation promoters which are known in principle to the skilled person.

Examples which may be mentioned here in further preferred embodiments are also one or more fatty acid salts in the active ingredient matrix, preferably sodium laurate, or further polymers such as, for example, ethyl-, methylcellulose, polyvinylpyrrolidone, tragacanth, bentonite, lactose, colloidal silicon dioxide. The amounts are from 1 to 50% by weight, preferably between 2 and 15% by weight.

Further preferred excipients of the present invention are for example silicone oil, glycerol esters of hydrogenated resin acids, hydroabietic alcohol resin esters, hydroabietic acid resin esters, hydrogenated methyl esters of terpentine resins, esters of partially hydrogenated terpentine resins, esters of terpentine resins.

An alternative possibility is additionally to employ also antioxidants such as tocopherols, butylated hydroxyanisole (BHA), gallic esters, butylated hydroxy-toluene (BHT), ascorbyl palmitate, ascorbyl stearate, for stabilization or minimizing the active ingredient degradation during storage.

Particularly suitable as backing layer are polyesters such as, for example, preferably polyethylene terephthalate (PET) and polybutylene terephthalate, which are distinguished by particular strength. In addition, virtually any other compatible plastics are suitable, such as, for example, polyvinyl chloride, ethylene-vinyl acetate, vinyl acetate, polyethylene, polypropylene, cellulose derivatives or combinations of different films.

Active ingredient patches of the invention which are particularly preferred are those composed of an active ingredient-containing matrix and backing layer on top, where the resulting TTS are, after application to the skin, transparent or at least translucent.

It may also be helpful for mechanical stabilization of the TTS additionally to employ a supporting layer, e.g. a nonwoven, the active ingredient dissolved or suspended in a solvent advantageously being applied to the nonwoven. Suitable nonwoven materials are known to a skilled person, preferably polyethylene terephthalate, cellulose, regenerated cellulose, cellulose nitrate or polyethylene.

The transdermal therapeutic systems of the invention are used for hormonal contraception, and for hormone replacement therapy.

The invention is explained in more detail by the following example, but without restricting the scope of the invention thereto.

A formulation was prepared on the laboratory scale and investigated for its human skin permeation:

| Composition based on the matrix | % by weight |
| --- | --- |
| norelgestromin | 3.50% |
| ethinylestradiol | 0.50% |
| DL-α-tocopherol | 0.40% |
| BIO PSA Q7-4302 | 82.60% |
| Kollidon 90 F USP | 3.00% |
| sodium laurate | 2.00% |
| diethylene glycol monoethyl ether | 8.00% |

Permeation of norelgestromin through epidermis of human skin is depicted in FIG. 1.

Figure 2:
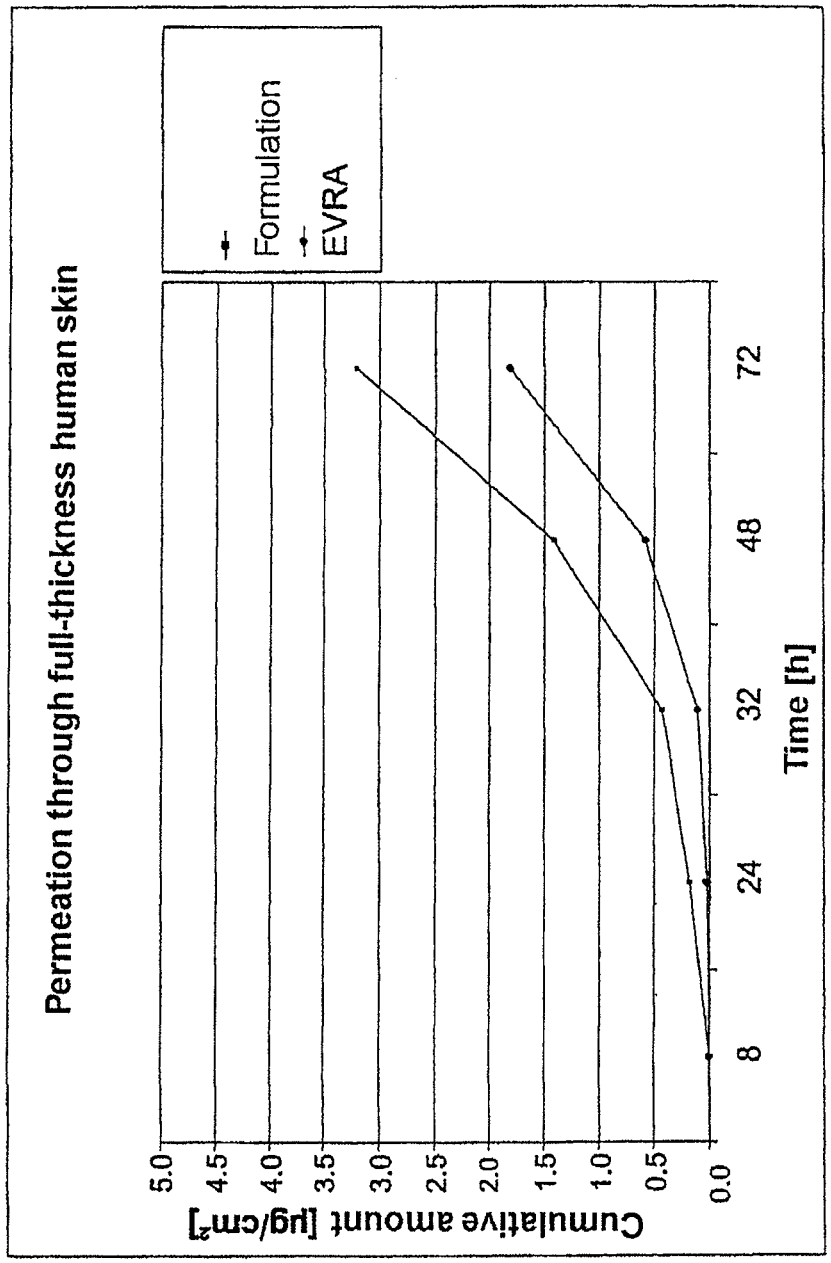
FIG. 2 depicts permeation of ethinylestradiol through full-thickness skin of human skin.

Permeation of ethinylestradiol through full-thickness skin of human skin is depicted in FIG. 2.

The formulation shows permeation results which are about twice as good as Ortho Evra™ TCS available on the market.

The invention claimed is:

1. A transdermal therapeutic system for administration of norelgestromin and ethinyl estradiol, the transdermal therapeutic system comprising:
   a norelgestromin and ethinyl estradiol-impermeable backing layer;
   at least one norelgestromin and ethinyl estradiol-containing matrix layer; and
   optionally a detachable protective layer;
   wherein the matrix layer is consisting of:
   a) a therapeutically effective dose of norelgestromin and ethinyl estradiol;
   b) a pressure-sensitive silicon adhesive;
   c) diethylene glycol monoethyl ether;
   d) DL-α-tocopherol;
   e) polyvinylpyrrolidone; and
   f) sodium laurate.

2. The transdermal therapeutic system as claimed in claim 1;
   wherein an application area of said system is smaller than 20 cm$^2$.

3. The transdermal therapeutic system as claimed in claim 1;
   wherein the transdermal therapeutic system is transparent or translucent.

4. The transdermal therapeutic system as claimed in claim 1, further comprising:
   a nonwoven supporting layer.

5. The transdermal therapeutic system as claimed in claim 4;

wherein the norelgestromin and ethinyl estradiol are dissolved or suspended in diethylene glycol monoethyl ether, and optionally norelgestromin and ethinyl estradiol are applied to the nonwoven.

6. The transdermal therapeutic system as claimed in claim 4;
wherein the nonwoven supporting layer consists of polyethylene terephthalate, regenerated cellulose, cellulose nitrate or polyethylene.

7. The transdermal therapeutic system as claimed in claim 1;
wherein the transdermal therapeutic system consists of a plurality of layers which differ in their composition and/or norelgestromin and ethinyl estradiol content.

8. A method of providing hormonal contraception to a patient in need thereof, the method comprising:
administering the transdermal therapeutic system of claim 1 to the patient.

9. A method of providing hormone replacement to a patient in need thereof, the method comprising:
administering the transdermal therapeutic system of claim 1 to the patient.

* * * * *